US006736640B1

(12) United States Patent
Ellenbecker

(10) Patent No.: US 6,736,640 B1
(45) Date of Patent: May 18, 2004

(54) APPARATUS FOR APPLYING SUCTION ADJACENT TO A TOOTH

(76) Inventor: John R. Ellenbecker, 2211 N. Jordan Ave., Juneau, AK (US) 99801

( * ) Notice: Subject to any disclaimer, the term of this patent is extended or adjusted under 35 U.S.C. 154(b) by 0 days.

(21) Appl. No.: 10/282,763

(22) Filed: Oct. 29, 2002

(51) Int. Cl.[7] ............................................. A61C 17/06
(52) U.S. Cl. .......................................... 433/93; 433/138
(58) Field of Search ............................ 433/93, 94, 140, 433/136, 138; 600/237, 238

(56) References Cited

U.S. PATENT DOCUMENTS

| 1,010,146 | A | 11/1911 | Ivory |
|---|---|---|---|
| 1,742,080 | A | 12/1929 | Jones |
| 2,644,234 | A | 7/1953 | Scott |
| 2,791,030 | A | 5/1957 | Tofflemire |
| 2,811,777 | A | 11/1957 | Tofflemire |
| 2,844,873 | A | 7/1958 | Bober |
| 2,885,783 | A | 5/1959 | Golden |
| 3,101,543 | A | 8/1963 | Baughan |
| D244,377 | S | 5/1977 | Sturdivant |
| 5,071,347 | A | 12/1991 | McGuire |
| 5,203,699 | A | 4/1993 | McGuire |
| 5,800,173 | A | 9/1998 | Heasley |

*Primary Examiner*—Ralph A. Lewis
(74) *Attorney, Agent, or Firm*—Leonard + Proehl, P.L.L.C.; Jeffrey A. Proehl

(57) ABSTRACT

An improved apparatus for applying suction adjacent to a tooth is disclosed. The apparatus comprises a suction conduit structure that includes a main conduit portion and a pair of secondary conduit portions extending from the main conduit portion. A pair of pad support members are positionable adjacent to lateral surfaces of the focus tooth, and each pad support member is mounted on one of the secondary conduit portions. A suction pad is mounted on each pad support member for positioning adjacent to the focus tooth. In one embodiment, a tooth gripping structure is mounted on each of the pad support members for gripping a lateral surface of an anchor tooth located next to the focus tooth of the patient. The tooth gripping structures extend toward each other. In another embodiment, a tooth engaging structure is mounted on each of the pad support members for engaging a jaw of the patient at a position of meeting of the focus tooth and an adjacent tooth.

20 Claims, 14 Drawing Sheets

APPARATUS FOR APPLYING SUCTION ADJACENT TO A TOOTH

BACKGROUND OF THE INVENTION

1. Field of the Invention

The present invention relates to dental suction devices and more particularly pertains to an improved apparatus for applying suction adjacent to a tooth for removing saliva from the operative area.

2. Description of the Prior Art

Various dental procedures require that the tooth being operated upon be maintained in a relatively dry condition during procedures such as adhesive composite restorations and applications of occusal sealants. The surfaces of the operative tooth must be isolated from moisture (e.g., saliva) so that the bonding of such adhesives or sealers is not negatively affected by the moisture. Dental dams have been used to isolate an individual tooth or a plurality of teeth from moisture, but can be difficult or painful to use on teeth that have not completely erupted from the gum of the patient. Unfortunately, dental sealants are preferably applied to a tooth prior to the complete eruption of the tooth for the most effective protection of the tooth, and this makes use of the dental dam for applications of these protective sealants difficult.

The use of dental suction devices is generally known in the prior art. Many of the known suction devices are intended to be used and reused after appropriate sterilization, and typically employ removable and replaceable gauze pads or rolls that may be replaced between the uses of the device, or even during the use of the device.

One very useful apparatus for applying suction adjacent to a tooth during dental procedures is disclosed in my U.S. Pat. No. 6,309,218. While the apparatus disclosed in that patent is effective, relatively simple to use, and is highly suitable for multiple usages with appropriate sterilization, it is believed that would be desirable to have an apparatus that is even simpler to make and use.

The improved apparatus for applying suction adjacent to a tooth according to the present invention substantially departs from the conventional concepts and designs of the prior art, and in so doing provides an apparatus primarily developed for the purpose of removing saliva from the operative area.

SUMMARY OF THE INVENTION

In view of the foregoing disadvantages inherent in the known types of dental suction devices now present in the prior art, the present invention provides a new improved apparatus for applying suction adjacent to a tooth construction wherein the same can be utilized for removing saliva from the operative area.

To attain this purpose, the present invention generally comprises a suction conduit structure that includes a main conduit portion and a pair of secondary conduit portions extending from the main conduit portion. A pair of pad support members are positionable adjacent to lateral surfaces of the focus tooth, and each pad support member is mounted on one of the secondary conduit portions. A suction pad is mounted on each pad support member for positioning adjacent to the focus tooth. In one embodiment, a tooth gripping structure is mounted on each of the pad support members for gripping a lateral surface of an anchor tooth located next to the focus tooth of the patient. The tooth gripping structures extend toward each other. In another embodiment, a tooth engaging structure is mounted on each of the pad support members for engaging a jaw of the patient at a position of meeting of the focus tooth and an adjacent tooth.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

One significant advantage of the present invention is the relatively simplicity of the apparatus that permits the apparatus to be formed of disposable materials such that it may be disposed after use. Further, the apparatus may employ one of a number of structures that mount the apparatus on one or more teeth of the patient to keep the apparatus temporarily in position during the dental procedure.

Further advantages of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects of the invention will become apparent when consideration is given to the following detailed description thereof. Such description makes reference to the annexed drawings wherein.

DESCRIPTION OF PREFERRED EMBODIMENTS

Figure 1:
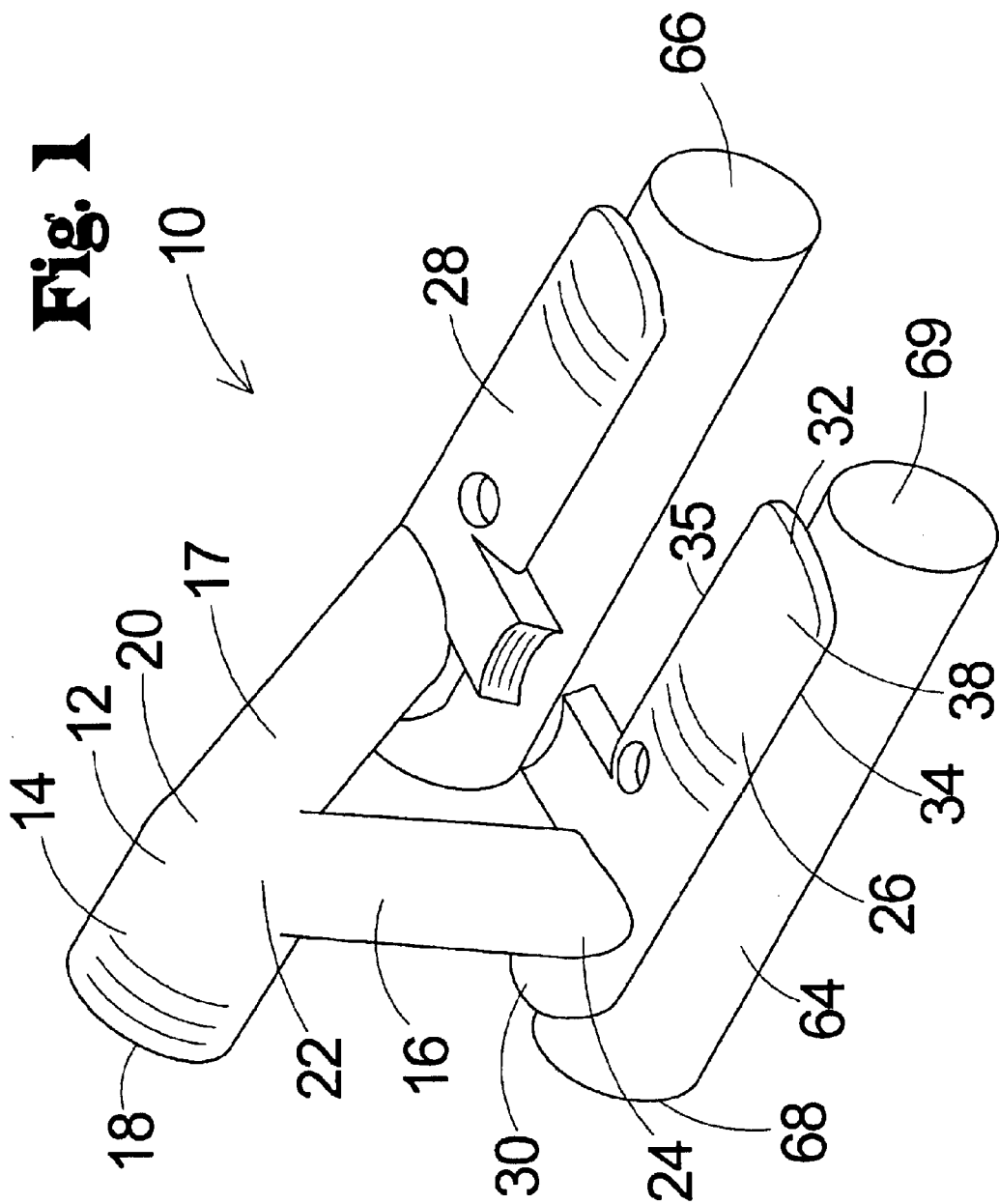
FIG. 1 is a schematic perspective view of an improved apparatus for applying suction adjacent to a tooth according to the present invention, and employing a tooth gripping structure.
Figure 2:
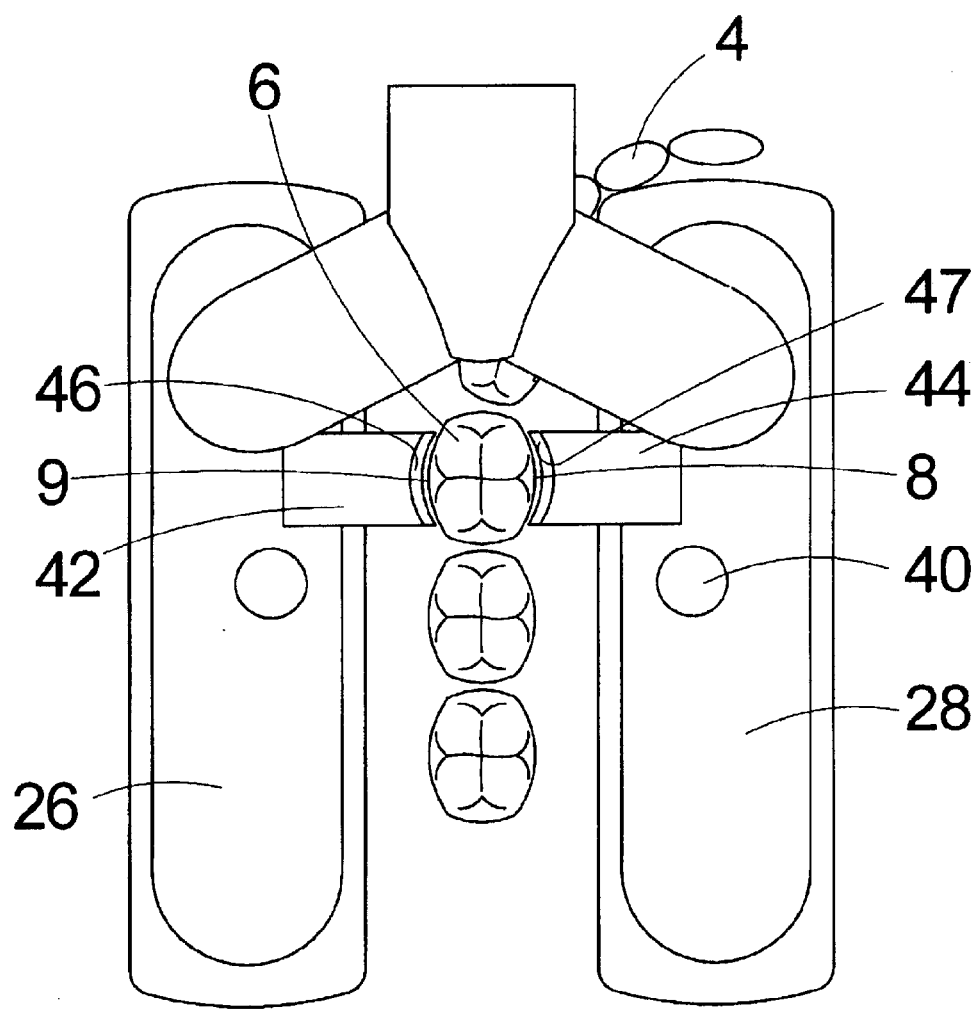
FIG. 2 is a schematic top view of the present invention.
Figure 3:
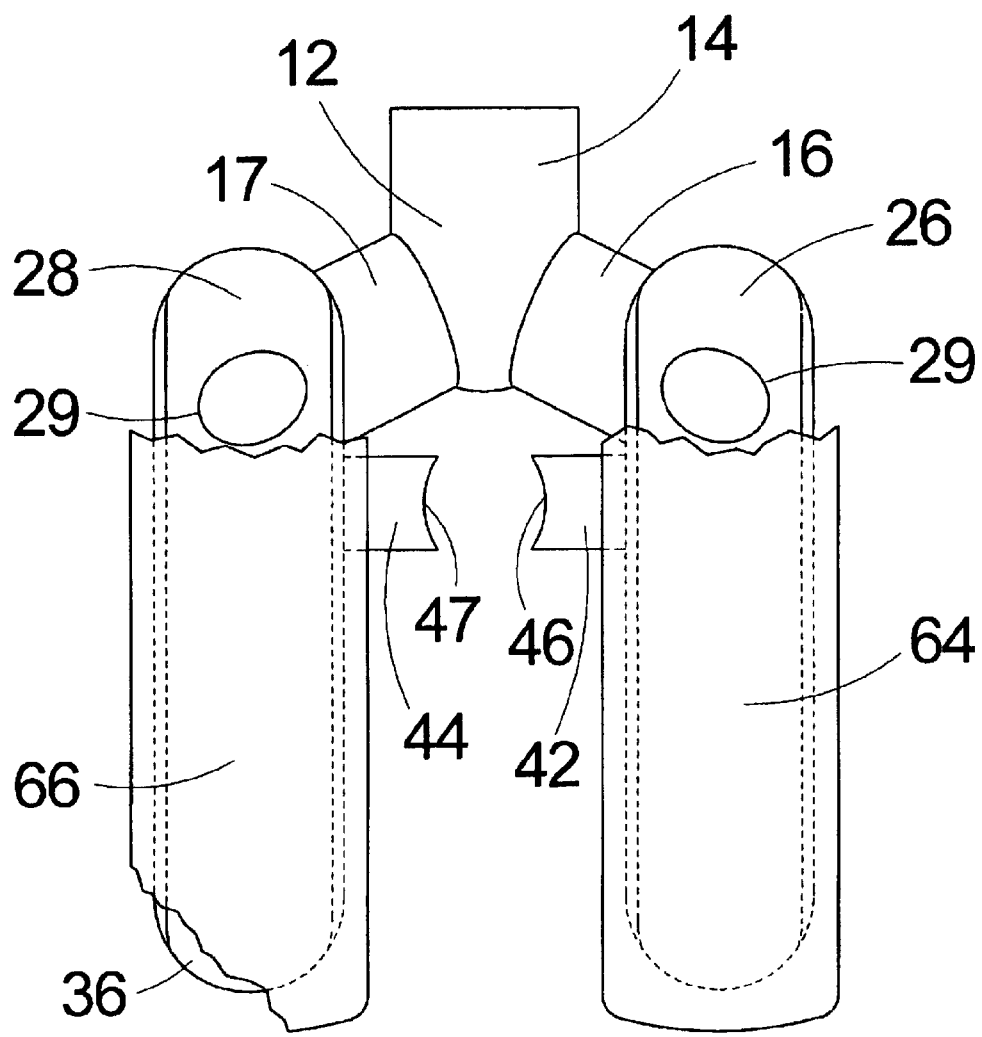
FIG. 3 is a schematic bottom view of the present invention.
Figure 4:
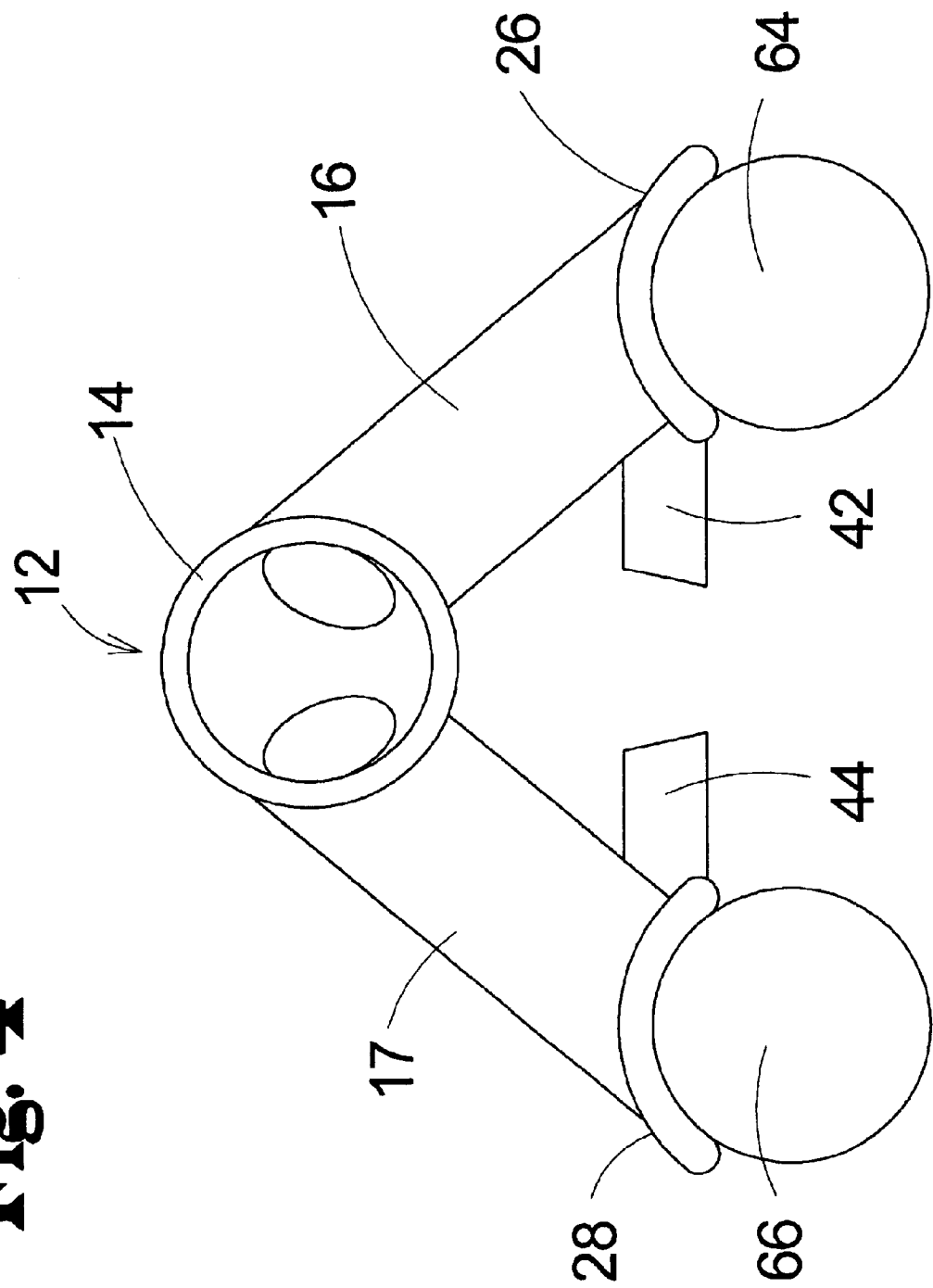
FIG. 4 is a schematic rear view of the present invention.
Figure 5:
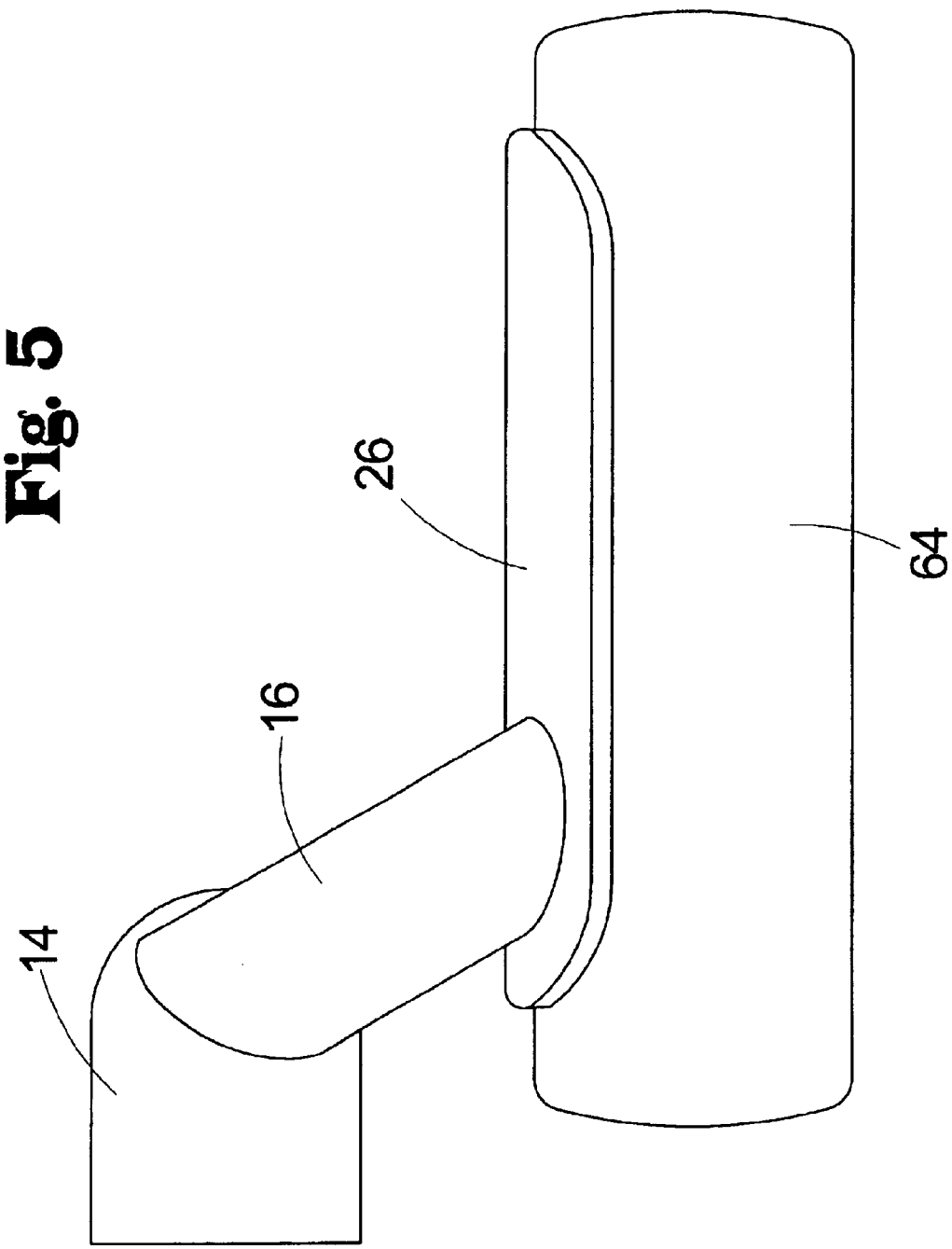
FIG. 5 is a schematic side view of the present invention.
Figure 6:
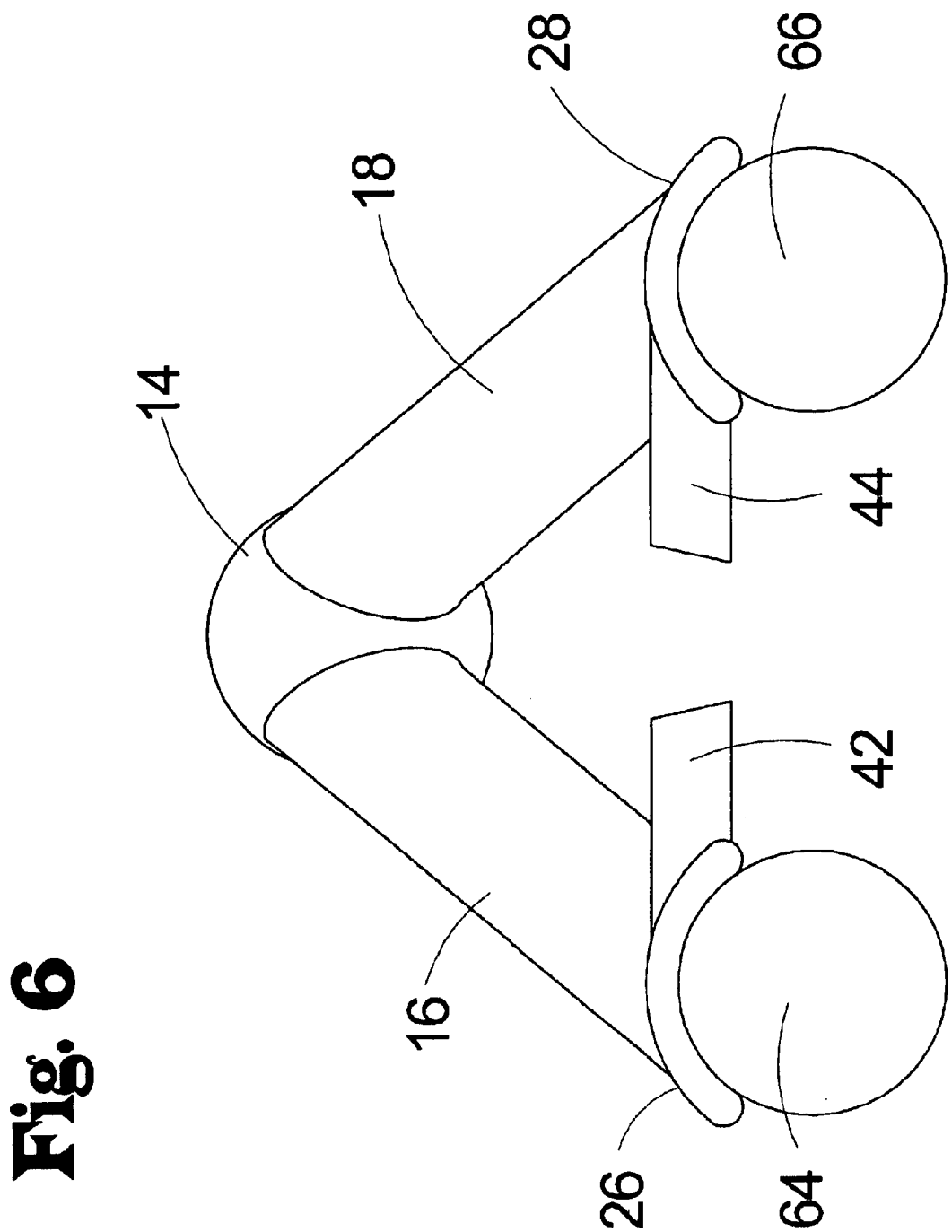
FIG. 6 is a schematic front view of the present invention.
Figure 7:
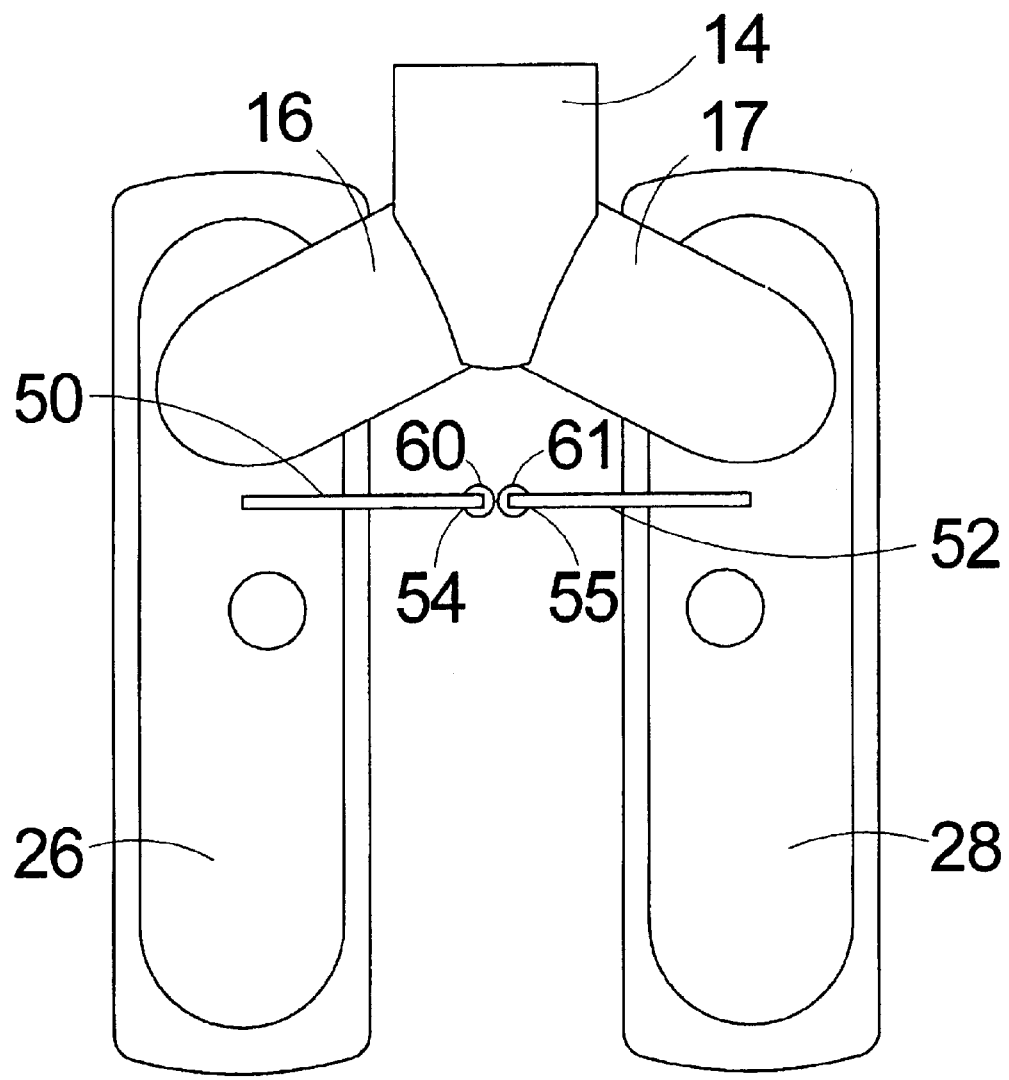
FIG. 7 is a schematic top view of the present invention having a first version of the tooth engaging structure.
Figure 8:
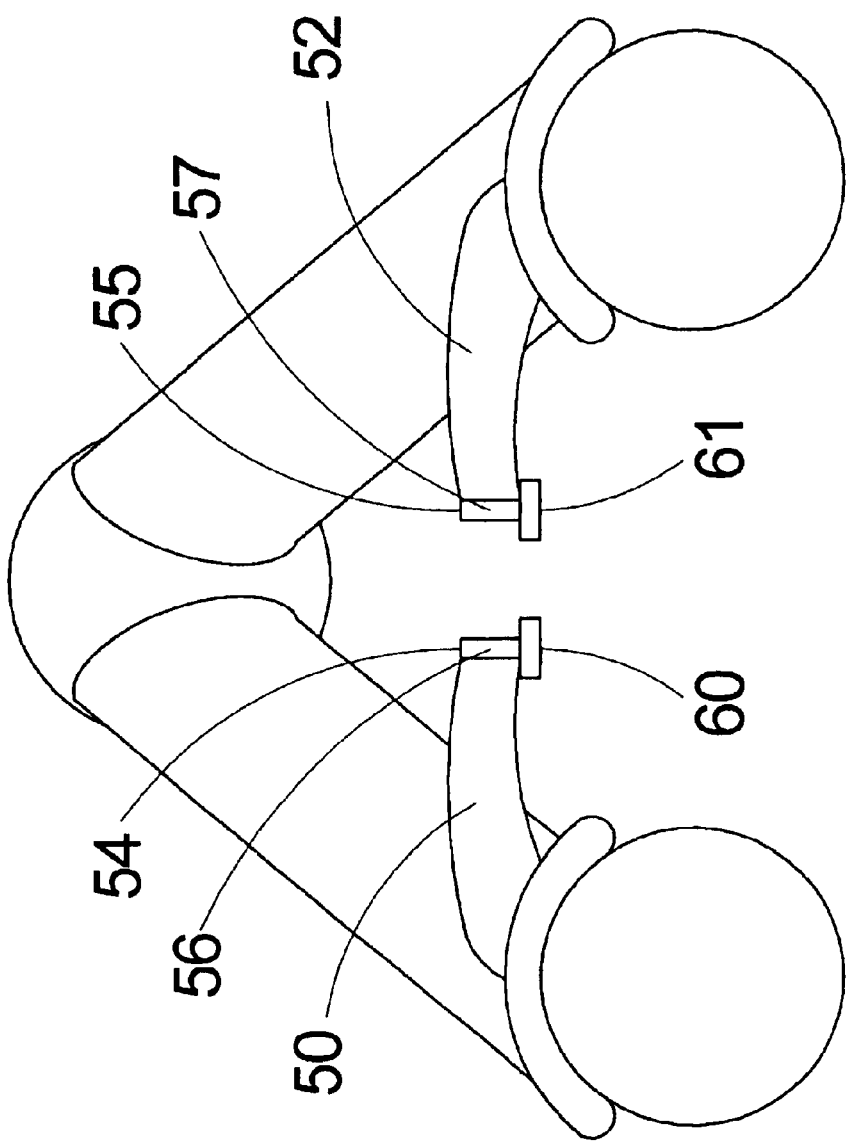
FIG. 8 is a schematic front view of the embodiment of FIG. 7 of the present invention.
Figure 9:
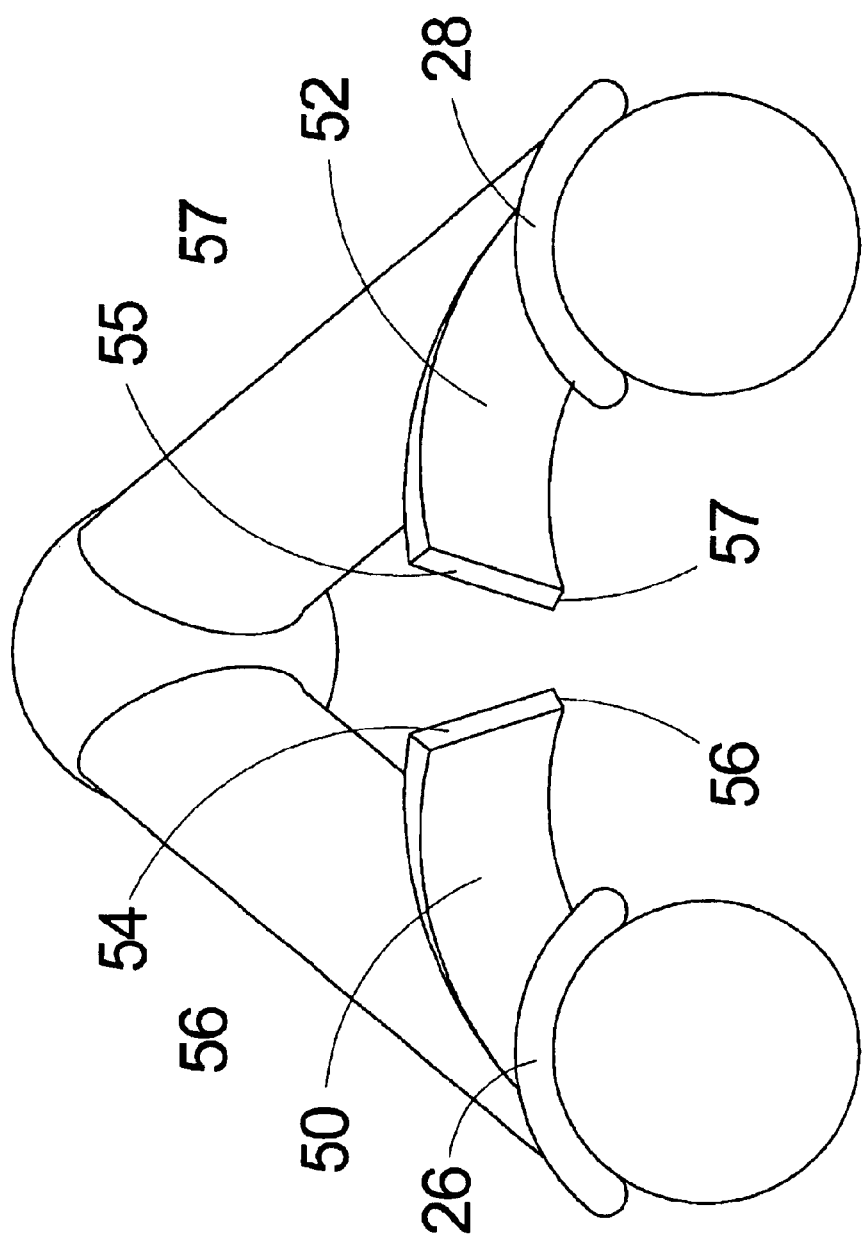
FIG. 9 is a schematic front view of a second version of the tooth engaging structure of the present invention.
Figure 10:
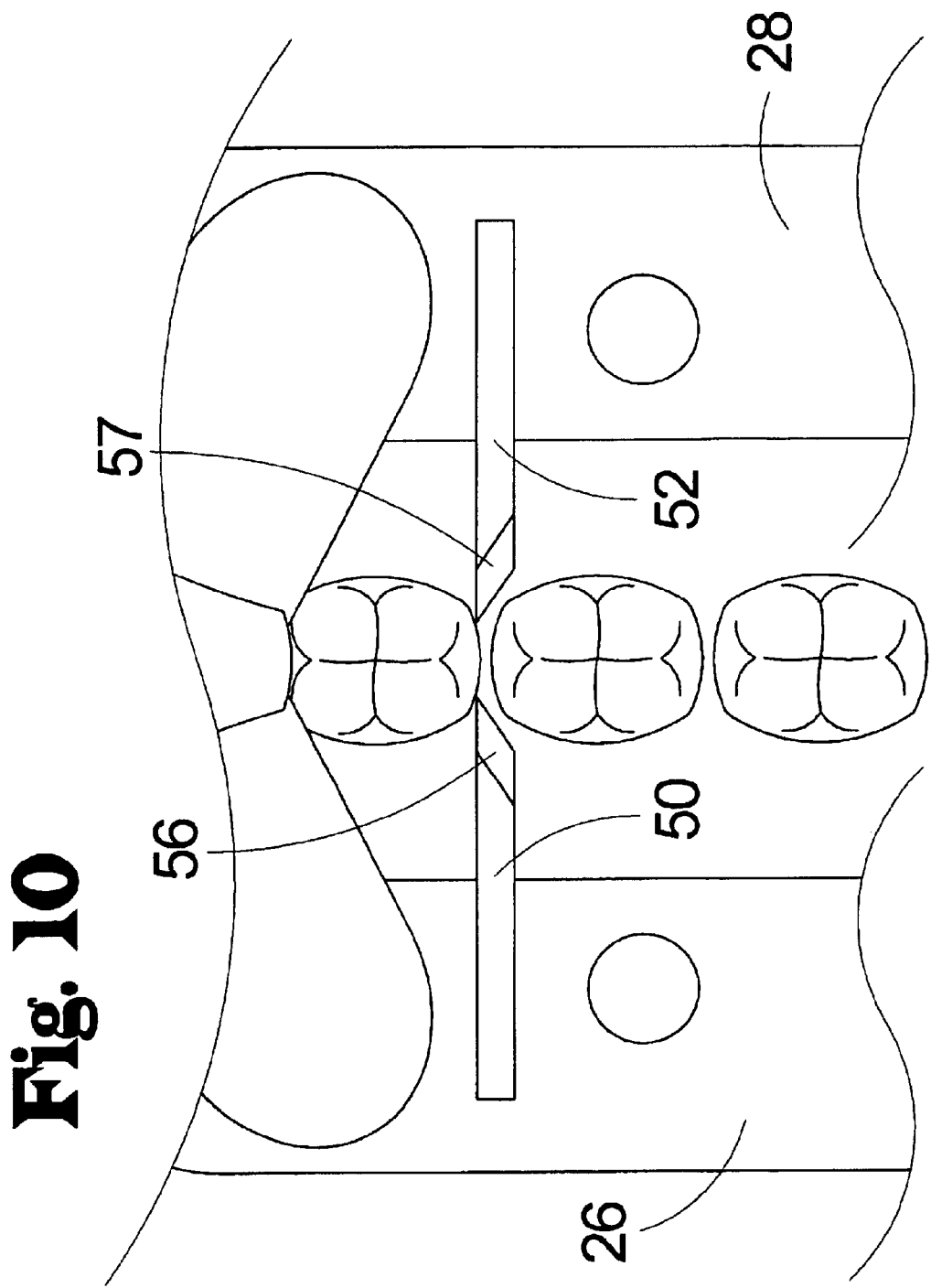
FIG. 10 is a schematic top view of the tooth engaging structure of FIG. 9.
Figure 11:
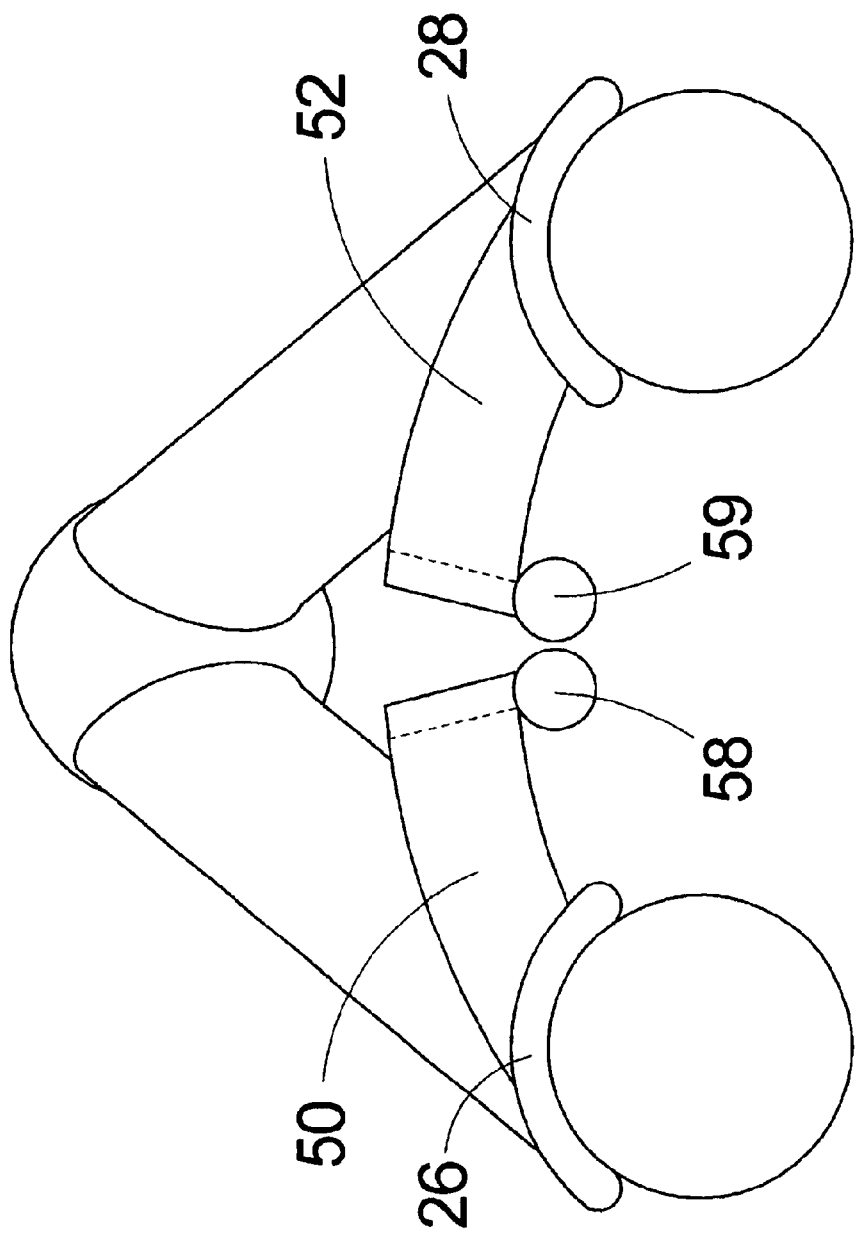
FIG. 11 is a schematic front view of a third version of the tooth engaging structure of the present invention.
Figure 12:
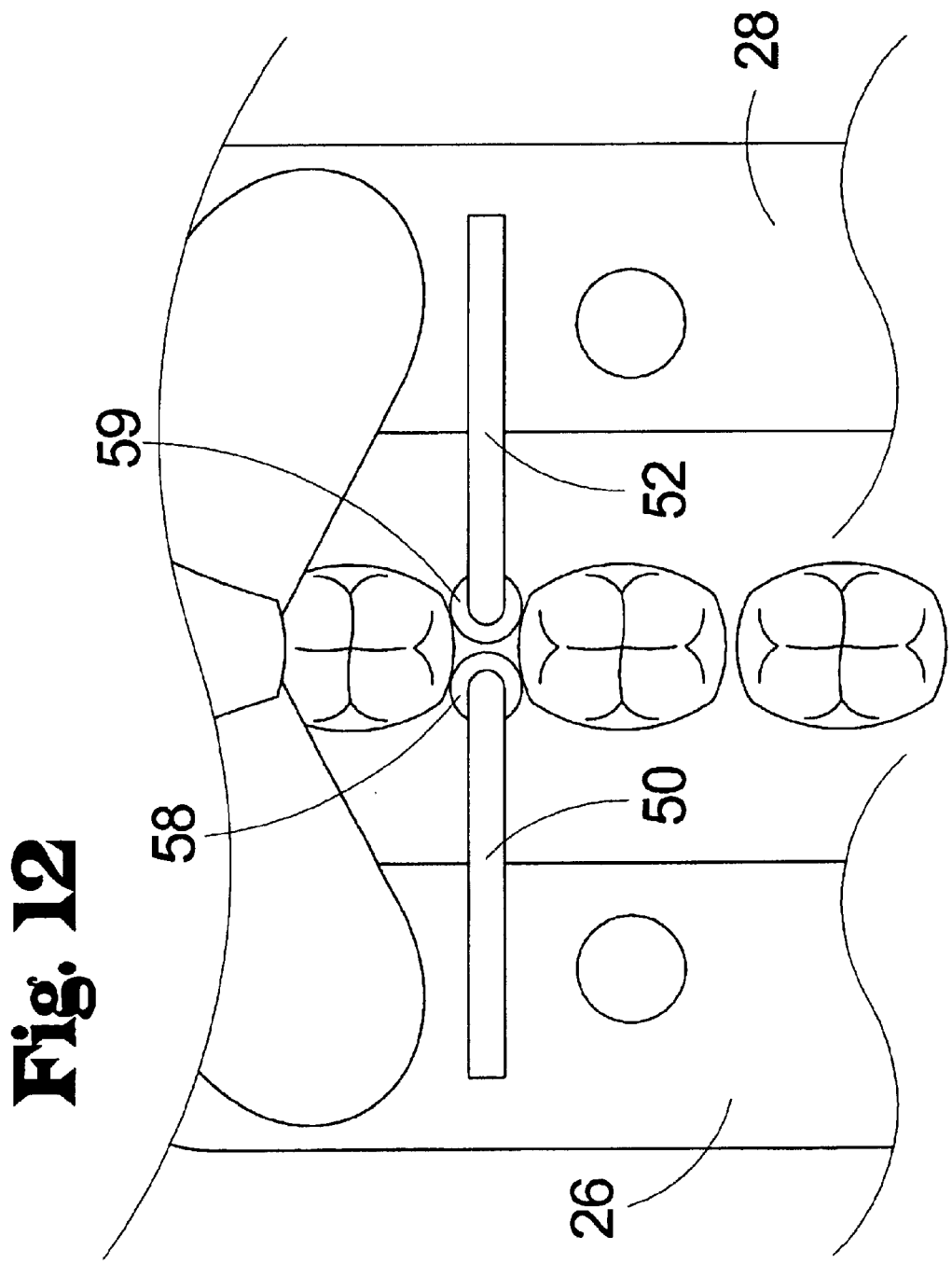
FIG. 12 is a schematic top view of the tooth engaging structure of FIG. 11.
Figure 13:
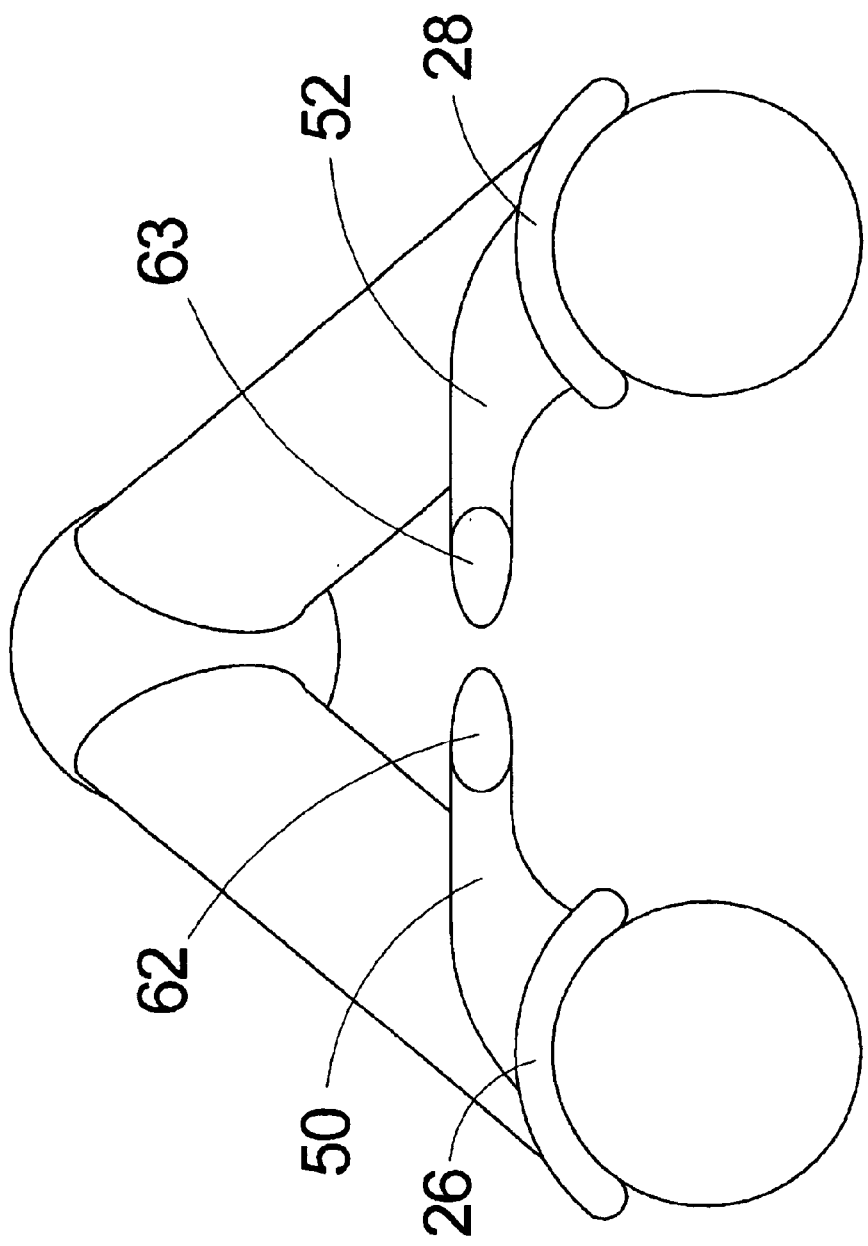
FIG. 13 is a schematic front view of a fourth version of the tooth engaging structure of the present invention.
Figure 14:
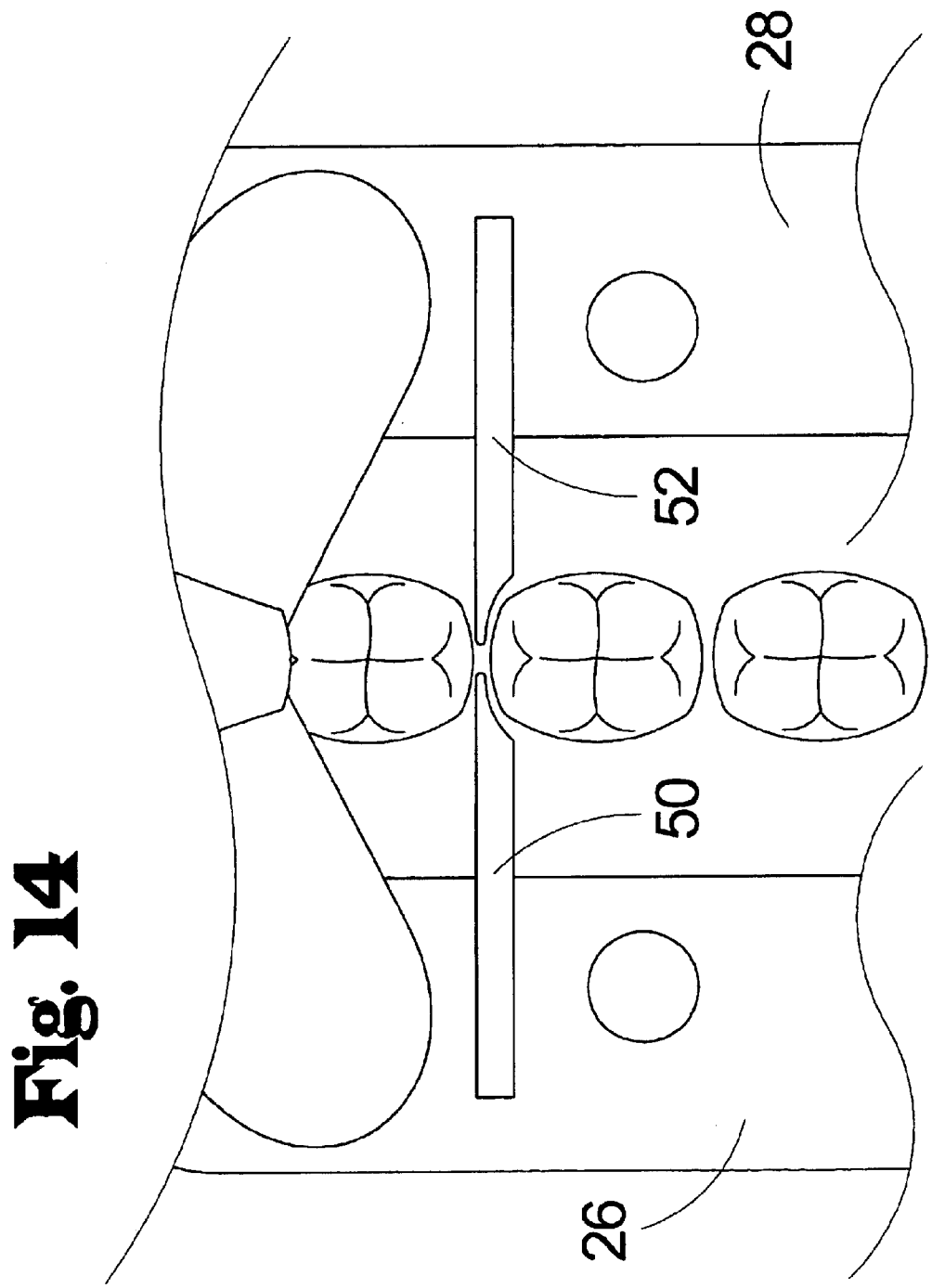
FIG. 14 is a schematic top view of the tooth engaging structure of FIG. 13.

With reference now to the drawings, and in particular to FIGS. 1 through 14 thereof, a new improved apparatus for applying suction adjacent to a tooth embodying the principles and concepts of the present invention and generally designated by the reference numeral 10 will be described.

The invention includes an apparatus for facilitating isolation or shielding of a focus tooth 2 of a patient from saliva during dental procedures. Illustratively, the focus tooth 2 is one of a plurality of teeth oriented in an arcuate line 4 in a patient's mouth, such as in the maxillary or the mandibular arch. At least one anchor tooth 6 in the arcuate line is located adjacent to the focus tooth 2. Each of the teeth has an inner lateral surface 8 facing inwardly from the arcuate line and each tooth has an outer lateral surface 9 facing outwardly from the arcuate line. Further, the focus tooth 2 and the anchor tooth 6 have a point or position of meeting or abutment between the teeth 2, 6.

As best illustrated in the Figures, the improved apparatus 10 for applying suction adjacent to a tooth generally comprises a suction conduit structure 12, a pair of pad support members 26, 28, and a pair of tooth gripping structures 42, 44 or a pair of tooth engaging structures 50, 52.

The suction conduit structure 12 of the invention may include a main conduit portion 14 for connecting to a suction source and a pair of secondary conduit portions 16, 17 branching off of the main conduit portion. The pair of secondary conduit portions 16, 17 each extend from the main conduit portion 14. The main conduit portion 12 has inlet end 18 and an outlet end 20, and the secondary conduit portions 16, 17 are mounted on and extend from the outlet end of the main conduit portion. Each of the secondary conduit portions 16, 17 has a first end 22 mounted on the main conduit portion 14 and a second end 24. The pair of secondary conduit portions 16, 17 may converge toward each other toward their first ends 22 and diverge away from each other toward their second ends 24. Each of the conduit portions 14, 16, 17 has a lumen, and the lumens of the secondary conduit portion 16, 17 are in fluid communication with the lumen of the main conduit portion 14.

The apparatus 10 also includes a pair of pad support members 26, 28 for positioning adjacent to lateral surfaces of the tooth or teeth. Each of the pad support members 26, 28 is mounted on, and may primarily supported by, one of the secondary conduit portions 16, 17. Further, each of the pad support members 26, 28 has an aperture 29 formed therein, and the lumen of each of the secondary conduit portions is in fluid communication with the aperture 29 of the respective pad support member to which the secondary conduit portion is mounted. Each of the secondary conduit portions 16, 17 may terminate at the respective pad support member 26, 28 such that the secondary conduit portions do not extend through or beyond the respective pad support member.

Each of the pad support members 26, 28 has a proximal end 30 and a distal end 32. Each of the pad support members 26, 28 may be connected to one of the secondary conduit portions 16, 17 at a location that is adjacent to the proximal end 30 of the pad support member, so that the pad support member extends away from the suction conduit structure. The pad support members 26, 28 may also extend in a substantially parallel relationship to a longitudinal axis of the main conduit portion 14, and the pad support members may extend in a substantially parallel relationship to each other. Each of the pad support members 26, 28 may have a pair of lateral edges 34, 35, and the lateral edges may be oriented substantially parallel to each other.

Each of the pad support members 26, 28 has a lower surface 36, and the lower surface may be generally concave or curved about an axis that extends substantially in the same direction as the longitudinal axis of the respective pad support member. Each of the pad support members 26, 28 has an upper surface 38, which may be generally convex such that the pad support member has a generally uniform thickness. The pad support members 26, 28 may substantially lie in a common plane, and the common plane of the pad support member may be located below the longitudinal axis of the main conduit portion 14.

Further, each of the pad support members 26, 28 may have a hole 40 for being engaged by a clamp forceps to help to slightly move the pad support members away from each other during mounting and dismounting of the apparatus 10 in the patient's mouth. It should be realized that such assistance by a separate tool is not critical to the mounting and dismounting of the apparatus in the mouth, especially in embodiments of the invention in which the apparatus is formed of a relatively flexible but resilient material. The hole 40 may be located substantially centrally between the proximal 30 and distal 32 ends of the respective pad support member.

Significantly, the main 14 and secondary 16, 17 conduit portions form a structural support for supporting the pad support members 26, 28 in their positions with respect to each other, and thus additional structures for supporting the pad support members is unneeded.

In one embodiment of the invention, a tooth gripping structure 42, 44 (see generally FIGS. 1 through 6) is mounted on each of the pad support members 26, 28 for gripping one of the lateral surfaces 8, 9 of the anchor tooth of the patient. Each of the tooth gripping structures 42, 44 extend toward each other from the pad support members 26, 28. Each of the tooth gripping structures 42, 44 has an inward edge 46, 47 for engaging the anchor tooth. The inward edge 46, 47 of each of the tooth gripping structures 42, 44 are oriented toward a central longitudinal axis of the main conduit portion 14 of the suction conduit structure 12 and toward the inward edge of the other of the tooth gripping structures. The inward edge 46, 47 of each of the tooth engaging structures may be substantially concave for extending along a portion of and embracing the lateral surfaces 8, 9 of the anchor tooth.

In another embodiment of the invention, the apparatus 10 of the invention may also include a tooth engaging structure 50, 52 (see generally FIGS. 7 through 14) mounted on each of the pad support members for engaging a pair of the patient's teeth at the point of meeting of the teeth. One benefit of using this structure 50, 52 for securing the apparatus in the mouth of the patient includes the ability to temporarily and slightly spread or wedge apart the adjacent teeth for facilitating interproximal dental work such as fillings. The tooth engaging structures 50, 52 are also less likely to need to be sized to the patient's teeth, as the tooth engaging structures do not extend about one or more teeth, but instead are designed to engaging the adjacent teeth at their point of adjacency or abutment, which is less sensitive to the patient's tooth size. Each of the tooth engaging structures 50, 52 may lie substantially in a common plane, and the common plane may extend substantially perpendicular to a plane in which the pair of pad support members 26, 28 lie. The common plane may also extend substantially perpendicular to a longitudinal axis of the main conduit portion 14 of the suction conduit structure 12.

Each of the tooth engaging structures 50, 52 may terminate in an end 54, 55. Each of the ends 54, 55 may be substantially linear. The linear end 54 of a first one 50 of the tooth engaging structures may lie along a line oriented at an angle to a line of the linear end 55 of a second one 52 of the tooth engaging structures, and the lines may converge at a point located at or above the plane in which each of the pair of pad support members 26, 28 lie, and in one embodiment the lines converge substantially at a point in the plane of the pair of pad support members.

Each of the ends 54, 55 may have a lower termination 56, 57. In one embodiment of the invention, the lower termination 56, 57 of each of the tooth gripping structures includes a ball 58, 59 (see FIGS. 11 and 12). In another embodiment of the invention, the lower termination 56, 57 of each of the tooth gripping structures includes a disc 60, 61 (see FIGS. 7 and 8). The disc 60, 61 may extend in a plane oriented substantially perpendicular to the line of the end 54, 55 of the tooth engaging structure 42, 44. In one embodiment of the invention, a thickness of the end 54, 55 of each of the tooth engaging structures 50, 52 is beveled thinner along a length of the linear end to create a wedge. In another embodiment, each of the tooth engaging structures 50, 52 terminates in an end point 62, 63 (see FIGS. 13 and 14). In some embodiments of the tooth engaging structures 50, 52, the lower terminations 56, 57 of each of the tooth engaging structures are biased together into contact and are resiliently spreadable away from each other to permit mounting on and removal from the teeth of the patient, and to also apply some degree of pressure against the teeth at their point of adjacency for wedging or lightly moving the teeth apart.

The apparatus of the invention also includes a pair of suction pads 64, 66 for positioning adjacent to one of the lateral sides 8, 9 of the anchor tooth 6, and the focus tooth 2. Each of the suction pads 64, 66 may be mounted on one of the pad support members 26, 28. Each of the suction pads 64, 66 may be adhered to the lower surface 36 of one of the pad support members 26, 28. The adhering of the suction pad may be accomplished through the use of a suitable adhesive material. Other pad mounting techniques are possible, but less desirable, and in some cases no particular connection between the pad and the pad support may be used, and the pad may simply be tucked between the pad support and a portion of the patient's mouth. Each of the suction pads 64, 66 may have a proximal end 68 and a distal end 69. The proximal end 68 of the suction pad 64, 66 may be positioned adjacent to the proximal end 30 of one of the pad support members 26, 28 and the distal end 69 of the suction pad may be positioned adjacent to the distal end 32 of the pad support member. Each of the suction pads 64, 66 may have a substantially cylindrical exterior shape, although other shapes may also be used, and each of the suction pads may be formed by an open cell foamed material permitting the flow of fluid therethrough.

In one preferred embodiment of the invention, the apparatus 10 is formed from a disposable material (such as, for example, a suitably strong and resiliently flexible plastic material), although a more permanent material (such as, for example, stainless steel) may also be used. The apparatus 10 may also be formed from a material that conducts light, so that light from a light source positioned adjacent to one portion of the apparatus is transmitted to another portion of the apparatus for illuminating the operative area of the patient's mouth.

In use, the pad support members of the apparatus may be incrementally spread apart so that the anchor tooth may be inserted in between the tooth gripping structures (with the central concave sections of the inward surfaces of the side members engaging the lateral surfaces of the anchor tooth), or so that the tooth engaging structures are positioned between the anchor and focus teeth. Illustratively, the application of a dental sealant to the partially erupted second adult molar (as the focus tooth) involves engaging the first adult molar as the anchor tooth. Suction is applied to the suction conduit structure so that saliva and other fluids absorbed by the suction pads are drawn through the secondary conduit portions and through the main conduit portion into the suction source. It as been found that with a suitable level of suction applied to the lumen of the suction conduit structure, excess saliva is readily drawn from the suction pads at a rate that allows the operative area to remain sufficiently free of excess saliva that might interfere with the process.

Illustratively, the suction pads may be provided in a variety of sizes, such as, for example, an extra small pad having a length of approximately 1.25 inches long (from proximal to distal ends) and a diameter of approximately $5/16$ inch, a small pad having a length of approximately 1.5 inches and a diameter of approximately $3/8$ inch, a medium pad having a length of approximately 1.75 inches and a diameter of approximately $7/16$ inch, and a large pad having a length of approximately of 2 inches and a diameter of approximately $1/2$ inch.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An apparatus for isolating a focus tooth of a patient from saliva during dental procedures, the apparatus comprising:

a suction conduit structure for applying suction adjacent to the tooth, the suction conduit structure including a main conduit portion for connecting to a suction source and a pair of secondary conduit portions, the pair of secondary conduit portions each extending from the main conduit portion;

a pair of pad support members for positioning adjacent to lateral surfaces of the focus tooth, each of the pad support members being mounted on one of the secondary conduit portions;

a pair of suction pads for positioning adjacent to the lateral sides of the focus tooth, each of the suction pads being mounted on one of the pad support members; and a tooth gripping structure mounted on each of the pad support members for gripping a lateral surface of an anchor tooth located next to the focus tooth of the patient, each of the tooth gripping structures extending toward each other from the pad support members.

2. The apparatus of claim 1 wherein each of the tooth gripping structures has an inward edge for engaging the anchor tooth, the inward edge of each of the tooth gripping structures being oriented toward a central longitudinal axis of the main conduit portion of the suction conduit structure and toward the inward edge of the other of the tooth gripping structures.

3. The apparatus of claim 2 wherein the inward edge of each of the tooth engaging structures is substantially concave.

4. The apparatus of claim 1 wherein each of the secondary conduit portions terminates at a respective one of the pad support members, a lumen of each of the secondary conduit portions being in fluid communication with an aperture in the respective pad support member.

5. The apparatus of claim 1 wherein each of the suction pads is adhered to a lower surface of one of the pad support members.

6. The apparatus of claim 1 wherein the main conduit portion has inlet end and an outlet end, and each of the secondary conduit portions is mounted on the outlet end of the main conduit portion, each of the conduit portions having a lumen, the lumen of the secondary conduit portion being in fluid communication with the lumen of the main conduit portion.

7. The apparatus of claim 1 wherein each of the pad support members has a proximal end and a distal end, and each of the pad support members is connected to one of the secondary conduit portions adjacent to a proximal end of the pad support member.

8. The apparatus of claim 7 wherein each of the pad support members has a hole for being engaged by a clamp forceps.

9. The apparatus of claim 1 wherein the pad support members lie substantially in a common plane being located below a longitudinal axis of the main conduit portion of the suction conduit structure.

10. An apparatus for isolating a focus tooth of a patient from saliva during dental procedures, the apparatus comprising:

a suction conduit structure for applying suction adjacent to the tooth, the suction conduit structure including a main conduit portion for connecting to a suction source and a pair of secondary conduit portions, the pair of secondary conduit portions each extending from the main conduit portion;

a pair of pad support members for positioning adjacent to lateral surfaces of the focus tooth, each of the pad support members being mounted on one of the secondary conduit portions;

a pair of suction pads for positioning adjacent to the lateral sides of the focus tooth, each of the suction pads being mounted on one of the pad support members; and a tooth engaging structure mounted on each of the pad support members for engaging a jaw of the patient at a position of meeting of the focus tooth and an adjacent tooth.

11. The apparatus of claim 10 wherein each of the tooth engaging structures lie substantially in a common plane.

12. The apparatus of claim 11, wherein the common plane extends substantially perpendicular to a plane in which the pair of pad support members lie.

13. The apparatus of claim 11 wherein the common plane extends substantially perpendicular to an axis of the main conduit portion of the suction conduit structure.

14. The apparatus of claim 10 wherein each of the tooth engaging structures terminates in an end, each of the ends being substantially linear, each of the ends having a lower termination.

15. The apparatus of claim 14 wherein the linear end of a first one of the tooth engaging structures lies along a line oriented at an angle to a line of the linear end of the tooth engaging structures, the lines converging at a point located at or above a plane in which each of the pair of pad support members lie.

16. The apparatus of claim 14 wherein the lower termination of each of the tooth gripping structures includes a ball.

17. The apparatus of claim 14 wherein the lower termination of each of the tooth gripping structures includes a disc.

18. The apparatus of claim 14 wherein a thickness of the end of each of the tooth engaging structures is beveled thinner along a length of the linear end.

19. The apparatus of claim 14 wherein the lower terminations of each of the tooth engaging structures are biased together into contact and are resiliently spreadable.

20. The apparatus of claim 10 wherein each of the tooth engaging structures terminates in an end point.

* * * * *